(12) United States Patent
Ströfer et al.

(10) Patent No.: US 7,193,115 B2
(45) Date of Patent: Mar. 20, 2007

(54) HIGHLY CONCENTRATED FORMALDEHYDE SOLUTION, PRODUCTION AND REACTION THEREOF

(75) Inventors: Eckhard Ströfer, Mannheim (DE); Martin Sohn, Mannheim (DE); Hans Hasse, Stuttgart (DE); Klemens Schilling, Stuttgart (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 228 days.

(21) Appl. No.: 10/494,762

(22) PCT Filed: Nov. 5, 2002

(86) PCT No.: PCT/EP02/12346

§ 371 (c)(1),
(2), (4) Date: Oct. 8, 2004

(87) PCT Pub. No.: WO03/040075

PCT Pub. Date: May 15, 2003

(65) Prior Publication Data

US 2005/0040359 A1    Feb. 24, 2005

(30) Foreign Application Priority Data

Nov. 5, 2001 (DE) ............... 101 54 187
Aug. 21, 2002 (DE) ............... 102 38 248

(51) Int. Cl.
*C07C 47/00* (2006.01)
*A23J 7/00* (2006.01)

(52) U.S. Cl. ......................... 568/422; 252/1

(58) Field of Classification Search ............ None
See application file for complete search history.

(56) References Cited

U.S. PATENT DOCUMENTS 6,610,888 B1   8/2003   Stroefer et al.

FOREIGN PATENT DOCUMENTS

EP   1 063 221   12/2000
GB   1190682   5/1970

OTHER PUBLICATIONS

Ullmann's Encyclopedia of Industrial Chemistry, Edition 2000 electronic release, Formaldehyde; Chapter 2 (physical properties), 2.2 Laqueous solutions).

*Primary Examiner*—Sikarl A. Witherspoon
(74) *Attorney, Agent, or Firm*—Novak Druce & Quigg LLP

(57) ABSTRACT

In an aqueous formaldehyde solution comprising formaldehyde in the form of monomeric formaldehyde, methylene glycol and polyoxymethylene glycols in a total concentration x of ≧65% by weight, the mean molar mass $\overline{M}$ of the polyoxymethylene glycols is, as a function of the formaldehyde concentration, equal to or less than the values given by equation I:

$$\left(\frac{\overline{M}}{\text{g/mol}}\right) = 48 + 6.589 \cdot 10^{-1} \cdot \left(\frac{x}{\%\ \text{by weight}}\right) + 4.725 \cdot 10^{2} \cdot \left(\frac{x}{\%\ \text{by weight}}\right)^{2} - 3.434 \cdot 10^{-3} \cdot \left(\frac{x}{\%\ \text{by weight}}\right)^{3} + 9.625 \cdot 10^{-5} \cdot \left(\frac{x}{\%\ \text{by weight}}\right)^{4} - 1.172 \cdot 10^{6} \cdot \left(\frac{x}{\%\ \text{by weight}}\right)^{5} + 5.357 \cdot 10^{-9} \cdot \left(\frac{x}{\%\ \text{by weight}}\right)^{6}$$ (I)

where:
$\overline{M}$ is the mean molar mass, and
x is the total concentration of formaldehyde in the form of monomeric formaldehyde, methylene glycol and polyoxymethylene glycols in % by weight (total formaldehyde concentration).

14 Claims, 2 Drawing Sheets

HIGHLY CONCENTRATED FORMALDEHYDE SOLUTION, PRODUCTION AND REACTION THEREOF

CROSS REFERENCE TO RELATED APPLICATIONS

This application is a national stage application under 35 U.S.C. § 371 of International Application No. PCT/EP02/12346, filed Nov. 5, 2002.

The present invention relates to aqueous formaldehyde solutions comprising formaldehyde in the form of a mixture of monomeric formaldehyde, methylene glycol and polyoxymethylene glycols, a process for their preparation, a process for preparing reaction products using the aqueous formaldehyde solutions of the present invention and the use of the aqueous formaldehyde solutions of the present invention. Formaldehyde is an important industrial chemical and is used for the production of numerous industrial products and consumer goods. Over 50 branches of industry at present use formaldehyde, mostly in the form of aqueous solutions or formaldehyde-containing synthetic resins. Commercially available, aqueous formaldehyde solutions have total concentrations of from 20 to 55% by weight of formaldehyde in the form of monomeric formaldehyde, methylene glycol and polyoxymethylene glycols. As a result, industrial syntheses which use aqueous formaldehyde solutions are encumbered by a large amount of water which is introduced together with the formaldehyde and is generally not required in the synthesis. This high water load determines the size of the reactors, their periphery and the work-up of the products. Furthermore, the excess water has to be treated and disposed of as wastewater. It may be necessary to separate off the water thermally, which consumes a great deal of energy. It is therefore desirable to reduce the water load in syntheses which require the use of aqueous formaldehyde solutions by using aqueous formaldehyde solutions which are as highly concentrated as possible.

However, the preparation and use of such high-concentration aqueous formaldehyde solutions is problematical since precipitation of solids occurs in the case of relatively highly concentrated solutions, in particular at low temperatures. Aqueous formaldehyde solutions containing more than 30% by weight of formaldehyde become turbid on storage even at room temperature, since higher polyoxymethylene glycols ($HO(CH_2O)_nH$; $n \geq 8$) are formed and precipitate. (Ullmann's Encyclopedia of Industrial Chemistry, Edition, 2000 electronic release, Formaldehyde; chapter 2 (physical properties), 2.2 (aqueous solutions), page 2, third paragraph). Although the solubility of the products present in the aqueous formaldehyde solution increases at higher temperatures, undesirable formation of formic acid occurs as a result of the Cannizzaro reaction. High-concentration formaldehyde solutions produced, for example, by distillation at elevated temperatures and pressures have high formic acid contents and thus have low pH values.

The water load in syntheses which use formaldehyde can also be reduced by the use of formaldehyde in solid form as paraformaldehyde or trioxane, but these solid products are significantly more difficult to handle in process engineering terms and are significantly more expensive to produce than aqueous formaldehyde solutions.

GB 1,190,682 relates to a process for concentrating aqueous formaldehyde solutions by distillation under reduced pressure in at least one distillation step. In this process, it is essential that the distillation temperature in each distillation step is below the stability temperature of the concentrated solution and the distillation is continued only as long as no turbidity occurs in the solution. Subsequent to each distillation step, the solution is subject to an aging phase in which the temperature is above the stability temperature of the concentrated solution. The stability temperature is the temperature below which polyoxymethylene glycols are precipitated. Aqueous formaldehyde solutions having concentrations of from 75 to 85% can be prepared by this process. This process is very complicated since the high-concentration solutions are, according to the description, obtained by multiple concentration and aging steps. Furthermore, GB 1,190,682 gives no information as to how long the high-concentration solutions are stable and whether the time is sufficient to carry out further reactions using the concentrated solutions. In addition, GB 1,190,682 is concerned exclusively with distillation processes.

The European patent EP-A 1 063 221 describes a process for reacting a solution which comprises a mixture of at least two chemical compounds which are in chemical equilibrium with one another with a solution of at least one further chemical compound, with the solution of the materials which are in chemical equilibrium being separated into two fractions having a nonequilibrium composition and being reacted with the other chemical compound before the chemical equilibrium is completely reestablished. Precise details of the chain length of the polyoxymethylene glycols and their proportion in the overall composition and also their influence on the time for which these solutions are stable are not given.

It is an object of the present invention to provide high-concentration formaldehyde solutions which are easy to handle and can be readily prepared in a single-stage or multistage process and can be used in syntheses which are carried out using aqueous formaldehyde solutions so that the water load in these syntheses is reduced.

The achievement of this object starts out from aqueous formaldehyde solutions comprising formaldehyde in the form of monomeric formaldehyde, methylene glycol and polyoxymethylene glycols in a total concentration x of $\leq 65\%$ by weight.

In the high-concentration aqueous formaldehyde solutions of the present invention, the mean molar mass $\overline{M}$ of the polyoxymethylene glycols is, as a function of the formaldehyde concentration, equal to or less than the values given by equation I:

$$\left(\frac{\overline{M}}{\text{g/mol}}\right) = 48 + 6.589 \cdot 10^{-1} \cdot \left(\frac{x}{\% \text{ by weight}}\right) + 4.725 \cdot 10^2 \cdot \\ \left(\frac{x}{\% \text{ by weight}}\right)^2 - 3.434 \cdot 10^{-3} \cdot \left(\frac{x}{\% \text{ by weight}}\right)^3 + \\ 9.625 \cdot 10^{-5} \cdot \left(\frac{x}{\% \text{ by weight}}\right)^4 - 1.172 \cdot 10^6 \cdot \\ \left(\frac{x}{\% \text{ by weight}}\right)^5 + 5.357 \cdot 10^{-9} \cdot \left(\frac{x}{\% \text{ by weight}}\right)^6 \quad \text{(I)}$$

where:
$\overline{M}$ is the mean molar mass, and
x is the total concentration of formaldehyde in the form of monomeric formaldehyde, methylene glycol and polyoxymethylene glycols in % by weight (total formaldehyde concentration).

The equation I is valid for total concentrations x in the range from 0 to 95% by weight.

The mean molar mass $\overline{M}$ of the reaction products of the formaldehyde with water (methylene glycol and polyoxymethylene glycols) is, as a function of the formaldehyde concentration, equal to or less than the values in the following table which shows them for selected formaldehyde concentrations:

| x/% by weight[1] | $\overline{M}$ |
|---|---|
| 65 | 109.9 |
| 75 | 132.4 |
| 85 | 181.2 |

[1]Total formaldehyde concentration

The values at other temperatures and formaldehyde concentrations can be obtained using equation I. Preference is given to mixtures in which the values for the mean molar mass $\overline{M}$ of the reaction products of the formaldehyde with water are at least 5% below the values given by equation I. Particular preference is given to mixtures in which the values are at least 10% below those given by equation I, and very particular preference is given to mixtures in which the values are at least 20% below those given by equation I. The solutions of the present invention may further comprise other constituents such as stabilizers.

In a commercially available formaldehyde solution, on the other hand, the mean molar mass $\overline{M}$ of the polyoxymethylene glycols is, as a function of temperature and formaldehyde concentration, as shown in the following tables for selected concentrations:

Commercially available formaldehyde solutions

| X/% by weight[1] | $\overline{M}$ |
|---|---|
| 37 | 76.8 |
| 50 | 88.8 |

[1]Total formaldehyde concentration

| $X_{formaldehyde}$/% by weight[1] | $X_{methanol}$/% by weight[2] | $\overline{M}$ |
|---|---|---|
| 37 | 1.5 | 77 |
| 49 | 2 | 83 |

[1]Total formaldehyde concentration
[2]Total methanol concentration

The commercially available solutions as in the above tables may further comprise small amounts of other constituents such as stabilizers.

The mean concentration of the methylene glycol and of the polyoxymethylene glycols can be determined, for example, by $^1$H- or $^{13}$C-NMR spectroscopy using methods described in the literature [Hahnenstein, I., Albert, M., Hasse, H., Kreiter, C. G., Maurer, G., NMR Spectroscopic and Densimetric Study of Reaction Kinetics of Formaldehyde Polymer Formation in Water, Deuterium Oxide, and Methanol, Ind. Eng. Chem. Res. (1995) 34, 440–450]. The total formaldehyde concentration of an aqueous formaldehyde solution can be determined by customary methods described in the literature, for example sulfite titration [J. F. Walker, Formaldehyde, 2nd edition, Reinhold Publ. Comp., New York, 1953, p. 382 ff.].

The formaldehyde solutions of the present invention can be prepared simply, cheaply and in a short time. No aging of the solutions during their preparation is necessary, or aging is undesirable. Furthermore, the formaldehyde solutions of the present invention can be prepared either from equilibrium solutions or from nonequilibrium solutions.

The use of these novel high-concentration aqueous formaldehyde solutions makes it possible a) to reduce the proportion of inert components (water load) and thus increase the space-time yield (STY) and reduce the capital costs by use of smaller apparatuses,
b) to reduce the amount of wastewater obtained and
c) to save energy in any thermal process which may be necessary to separate off the water.

Thus, for example, the production of 26.2 t/h of methylenediphenyl diisocyanate (MDI) from 20.8 t/h of methanediphenyldiamine (MDA), corresponding to a 200 kt/a MDI plant, requires 8.2 t/h of 50% strength by weight aqueous formaldehyde solution. This corresponds to a water load of 4.1 t/h. The use of a 65% strength by weight aqueous formaldehyde solution enables this water load to be virtually halved to 2.2 t/h.

According to the present invention, it has been found that it is possible to provide formaldehyde solutions comprising formaldehyde in the form of monomeric formaldehyde, methylene glycol and polyoxymethylene glycols in a total concentration of ≧65% by weight at temperatures of generally from −5 to 150° C., preferably from 10 to 100° C., particularly preferably from room temperature to 50° C., without precipitation of solids occurring (freedom from solids). For the purposes of the present invention, freedom from solids means a solids content in the aqueous formaldehyde solutions of the present invention of generally <1% by weight, preferably <0.5% by weight, particularly preferably <0.1% by weight.

It has been found that precipitation of solids in high-concentration aqueous formaldehyde solutions can be avoided by reducing not the amount of the polyoxymethylene glycols, as has previously been assumed in the prior art, but their mean chain length (which correlates with the mean molar mass). In this way it is possible to provide high-concentration aqueous formaldehyde solutions which are stable (no precipitation of solids), even at temperatures at which precipitation of solids usually occurs in such high-concentration formaldehyde solutions, for sufficiently long for a reaction with appropriate compounds to be carried out.

For the purposes of the present invention, an aqueous formaldehyde solution is a formaldehyde solution which contains at least 5% by weight, preferably at least 10% by weight, of water.

These aqueous formaldehyde solutions of the present invention preferably display no precipitation of solids at temperatures of generally from −5 to 180° C., preferably from 10 to 100° C., particularly preferably from room temperature to 50° C., i.e. at temperatures at which the reactions with formaldehyde are usually carried out, for a period of at least 1 minute, preferably at least 5 minutes, particularly preferably at least 1 hour.

The aqueous formaldehyde solutions of the present invention can thus be used wherever reactions with appropriate compounds occur within the period described.

A further advantage of the solutions of the present invention is that they can have low formic acid concentrations even at a high total formaldehyde concentration. The pH of a commercially available 49% strength by weight formaldehyde solution (containing from 1.0 to 2.0% by weight of methanol as stabilizer) is usually from 3.0 to 3.5 at 50° C.

Solutions according to the present invention having significantly higher formaldehyde contents, e.g. 65% by weight, can have substantially higher pH values (e.g. from 4.0 to 6.0) and thus contain less formic acid.

The use of stabilizers to suppress the precipitation of solids, which stabilizers may interfere in chemical reactions, is not necessary in the case of the aqueous formaldehyde solutions of the present invention. However, it is possible to use stabilizers. In this case, any desired stabilizers can be used. If stabilizers are to be used, preference is given to using stabilizers selected from among alcohols, in particular methanol, ethanol, propanol or butanol, urea and melamine.

Since formaldehyde is highly reactive, this period of time is sufficient for the aqueous formaldehyde solutions of the present invention to be used in syntheses, preferably in syntheses which can be employed industrially.

The present invention thus makes it possible to provide high-concentration aqueous formaldehyde solutions which comprise formaldehyde in the form of monomeric formaldehyde, methylene glycol and polyoxymethylene glycols in a total concentration of $\geq 65\%$ by weight, preferably $\geq 70\%$ by weight, particularly preferably $\geq 75\%$ by weight.

The aqueous formaldehyde solutions of the present invention are prepared by removal of water or a water-containing mixture, preferably by rapid removal over a period of generally from 1 second to 5 hours, preferably from 5 seconds to 1 hour, particularly preferably from 10 seconds to 30 minutes. The novel aqueous formaldehyde solutions obtained can, surprisingly and contrary to the general consensus of the prior art, be kept for a period of time which is sufficiently long for a chemical reaction, generally at least 1 minute, preferably at least 5 minutes, particularly preferably at least 1 hour, without precipitation of solids occurring. In particular, no aging at elevated temperatures is necessary. In fact, an increase in the temperature is generally undesirable.

The preparation of the aqueous formaldehyde solutions of the present invention is carried out by the following process:

Separation of an aqueous formaldehyde solution comprising water and from 5 to 65% by weight of a starting mixture of formaldehyde in the form of monomeric formaldehyde, methylene glycol and polyoxymethylene glycols and optionally further components such as stabilizers into at least two fractions in which various compounds of the mixture are present in higher concentrations than in the starting mixture, where at least one of the two or more fractions is depleted in water compared to the starting mixture so that the formaldehyde in the form of monomeric formaldehyde, methylene glycol and polyoxymethylene glycols is present in a total concentration of $\geq 65\%$ by weight, preferably $\geq 70\%$ by weight, particularly preferably $\geq 75\%$ by weight.

The components of the aqueous formaldehyde solutions used can be either in equilibrium or not in equilibrium in the process of the present invention.

The two (or more) fractions are preferably a first, generally low-boiling, fraction comprising monomeric formaldehyde and methylene glycol and a second, generally higher-boiling, fraction comprising water, monomeric formaldehyde, methylene glycol and polyoxymethylene glycols. The first fraction further comprises the water removed from the aqueous formaldehyde solution.

The aqueous formaldehyde solutions of the present invention are obtained by means of appropriate separation methods.

In a preferred embodiment of the process of the present invention, separation is carried out by means of a separation method which comprises at least one step in which the aqueous formaldehyde solution is at least partly vaporized; a thermal separation occurs. The thermal-separation can be carried out in one or more stages, in cocurrent or in countercurrent. This can be achieved, for example, in a distillation apparatus.

In a particularly preferred embodiment of the process of the present invention, the removal of water or a water-containing mixture occurs rapidly. The removal occurs within a period of from 1 second to 5 hours, preferably from 5 seconds to 1 hour, particularly preferably from 10 seconds to 30 minutes.

The at least partial vaporization is particularly preferably carried out in the form of a single-stage vaporization. Suitable types of vaporizer are, for example, natural convection vaporizers, forced circulation vaporizers, climbing film evaporators, thin film evaporators and falling film evaporators and also stirred vessels. Preference is given to using a film evaporator in the process of the present invention. A suitable film evaporator is disclosed in, for example, EP-A 1 063 221. This is a thin film evaporator. Furthermore, preference is given to using a falling film evaporator in the process of the present invention.

In a further, preferred embodiment, the at least partial vaporization is carried out in a helical tube or coil tube evaporator. Suitable helical tube or coil tube evaporators are disclosed in Chem. Ing. Tech. 68 (6), 1996, pages 706 to 710, and in Chem. Ing. Tech. 42 (6), 1970, pages 349 to 354. When using a helical tube or coil tube evaporator, the starting solution is fed under pressure to a preheater, heated there and subsequently depressurized to form vapor. The solution is then concentrated to the end product in the subsequent heated helical tube.

The process of the present invention is particularly preferably carried out using a film evaporator selected from among thin film evaporators, helical tube or coil tube evaporators and falling film evaporators.

It is also possible to carry out the at least partial vaporization in a column, preferably in a reaction column. For example, a commercially available formaldehyde solution can be depressurized at a temperature of generally from −5 to 150° C., preferably from 10 to 100° C., very particularly preferably from room temperature to 50° C., in a reaction column, preferably by greatly reducing the pressure to which the solution is subjected, as a result of which the higher homologues of formaldehyde remain in the solution and monomeric formaldehyde, water and possibly methylene glycol are vaporized. In this vaporization method, the temperature is dependent on the pressure. The latter is generally from 1 mbar to 40 bar, preferably from 10 mbar to 11 bar, particularly preferably from 50 mbar to 1 bar.

It is likewise conceivable for the water to be removed from the formaldehyde solution by chemical reaction of a compound which is inert or relatively unreactive toward monomeric formaldehyde, methylene glycol and polyoxymethylene glycols with water, e.g. by a reaction in which water is consumed. For example, a reactive distillation process is conceivable.

Apart from the abovementioned separation methods involving distillation, adsorptive methods can also be used for the at least partial removal of the water, i.e. the separation in this method is achieved by adsorption. Drying by means of molecular sieves, preferably molecular sieves having pore sizes of from 3 to 10 Angstroem, is particularly useful. Extraction methods are less suitable. Crystallization methods which were examined were found to be unsuitable.

In one embodiment of the process of the present invention, the rapid evaporation of the low boilers is carried out in a film evaporator.

BRIEF DESCRIPTION OF THE DRAWINGS

The invention will now be more fully described by way of example with reference to the accompanying drawings in which:

FIG. 1 schematically shows the flow diagram of a process according to the present invention. In FIG. 1, the reference numerals have the following meanings:

Figure 1:
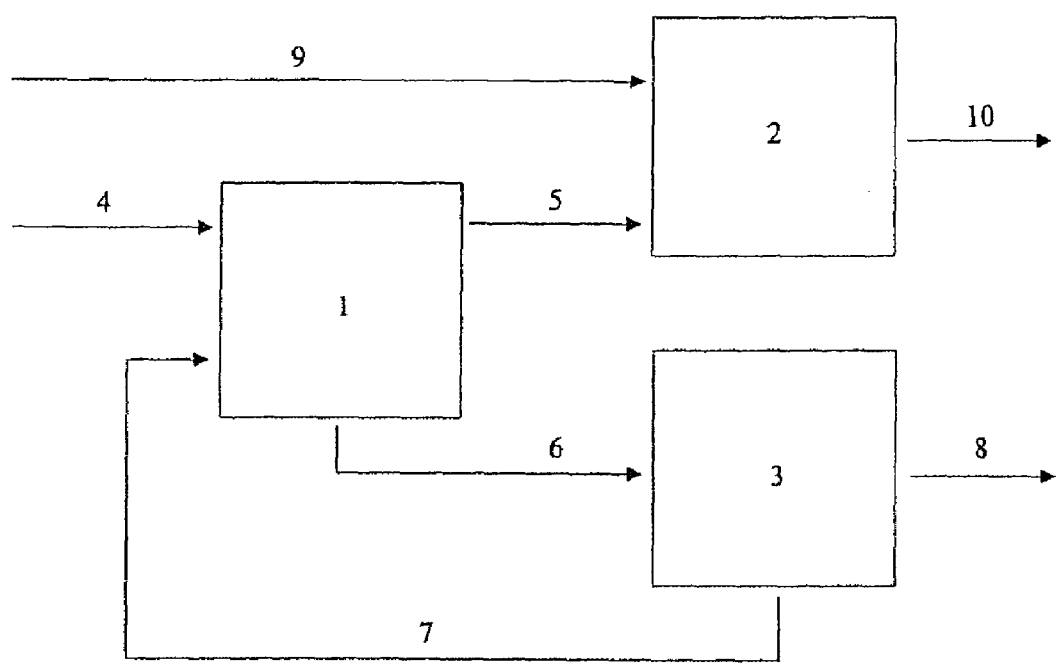
FIG. 1 is a flow diagram schematically illustrating a process according to the instant claims; and, FIG. 2 is a schematic illustration of a laboratory setup comprising a film evaporator for the preparation of high concentration formaldehyde solutions according to the instant claims.

1 film evaporator
2 main reactor system
3 separation apparatus
4 raw solution
5 desired fraction (aqueous formaldehyde solution according to the present invention)
6 residual fraction (low-boiling fraction)
7 recirculated solution
8 discharge stream
9 starting materials
10 products The apparatuses/streams 3, 7, 8 are optional.

A raw formaldehyde-containing aqueous solution 4, e.g. a commercial 20–55% strength by weight aqueous formaldehyde solution, is fed in via a feed line. This solution comprises a plurality of components which are generally but not necessarily in chemical equilibrium with one another, viz. water, monomeric formaldehyde (HCHO), methylene glycol ($CH_2(OH)_2$), which is formed from formaldehyde by reaction with water, and polyoxymethylene glycols (HO$(CH_2O)_n$H; where n=2–30), which are formed by condensation of the methylene glycol.

This raw solution 4 is fed to a film evaporator 1. In this, it is separated into a desired fraction 5 (aqueous formaldehyde solution according to the present invention) and a residual fraction 6 (low-boiling fraction comprising monomeric formaldehyde, possibly methylene glycol and water), preferably by rapid removal of water. The desired fraction (aqueous formaldehyde solution according to the present invention) is then generally fed to a main reactor system 2 where it is reacted with further starting materials 9 to form products 10.

The residual fraction 6 can in many cases be utilized further somewhere else in the overall processes. In this case, the apparatuses/streams 3, 7, 8 become superfluous. The residual fraction 6 can be particularly advantageously employed as scrubbing liquid in the absorber in customary processes for preparing formaldehyde from methanol where it advantageously replaces scrubbing water. If the residual fraction 6 is not to be used elsewhere as described above, the process shown in FIG. 1 is appropriate. In this, the fraction 6 is fed to a separation apparatus 3 in which water is removed by suitable means (e.g. by distillation or extraction) (water discharge 8). The solution 7 formed in this way is then mixed into the raw feed solution 4 and again introduced into the film evaporator 1. While short residence times are advantageous in the separation 1, the residence times in the separation 3 are not critical. In general, residence times as occur in industrial distillations (in the range from a few minutes to a number of hours) will be suitable. In fact, preference is given to long residence times. It is useful, but by no means necessary, to install residence containers between the apparatuses 1 and 3 or between 3 and 1 (streams 6 or 7).

Suitable operating conditions for a thermal separation in apparatus 1 are a temperature of generally from 5° C. to 150° C., preferably from 10° C. to 100° C., generally at an absolute pressure of from 0.1 mbar to 40 bar. When using a film evaporator, temperatures of from 20° C. to 100° C. at atmospheric pressure are particularly preferred. Apart from the thin film evaporator disclosed in EP-A 1 063 221, it is also possible to use a film evaporator without mechanical action on the liquid film on the evaporation surface. The heat transfer surface of such falling film or falling stream evaporators can be configured as tubes or plates. Various modes of operation of a film evaporator are described in EP-A 0 063 221 and in Chem. Ing. Tech. 42 (6), 1970, pages 349 to 354, and Chem. Ing. Tech. 68 (6), 1996, pages 706 to 710.

In the case of a separation in a distillation apparatus by single-stage or multistage vaporization, e.g. by flash evaporation, suitable temperatures are generally from 50 to 180° C., preferably from >100 to 180° C., generally at a pressure of from 0.2 bar to 10 bar, so that the preferred rapid removal of water is achieved.

Removal of water by adsorptive methods is generally carried out at from 5 to 100° C., preferably from 20 to 70° C., very particularly preferably at room temperature, preferably at from atmospheric pressure to 8 bar, particularly preferably at atmospheric pressure.

The aqueous formaldehyde solutions of the present invention have many possible applications. In principle, the aqueous formaldehyde solutions of the present invention can be used in any process in which an aqueous formaldehyde solution is required. Such use requires no significant process changes: it is simply necessary to replace the previously used formaldehyde solutions in order to gain the advantage of the reduced water load.

The present invention therefore also provides a process for preparing monomeric, oligomeric and polymeric reaction products of monomeric formaldehyde, methylene glycol and/or polyoxymethylene glycols with compounds (including formaldehyde itself) which react with monomeric formaldehyde, methylene glycol and/or polyoxymethylene glycols, wherein an aqueous formaldehyde solution according to the present invention is used.

Preferred compounds which react with monomeric formaldehyde, methylene glycol and/or polyoxymethylene glycols are selected from the group-consisting of:

Compounds containing amino groups, in the case of which Schiff bases are formed or a Mannich reaction is carried out. For example, amines react with the aqueous formaldehyde solutions of the present invention and hydrogen to form methylamines. Use of ammonia enables hexamethylenetetramines to be prepared, and reaction with ammonium chloride forms monomethylamine, dimethylamine or trimethylamine and formic acid, depending on the reaction conditions. Reaction of the aqueous formaldehyde solutions of the present invention with ammonia and ketones enables imidazoles to be prepared. Reaction with urea gives monotrimethylolurea, dimethylolurea and trimethylolurea, while reaction with melamine forms methylolmelamines, with melamine resins being formed by polycondensation of melamine with the aqueous formaldehyde solutions of the present invention.

Diols, which react with the aqueous formaldehyde solutions of the present invention to form cyclic ethers, for example dioxolane from glycol and the aqueous formaldehyde solutions of the present invention; also alcohols, thiols, carboxylic acids.

Aldehydes (including formaldehyde itself), in which case polyhydric alcohols such as sugars, pentaerythritol, trimethylolpropane and neopentyl glycol are formed by an aldol reaction.

Malonates or ketones (and also primary aldehydes) which have a $CH_2$ group next to the carbonyl group, in which case double bonds are formed, Hydroxylamines, hydrazines or semicarbazides, which form formaldehyde oximes and the corresponding hydrazones or semicarbazones.

Acetylene, which gives, in a Reppe addition, 2-butyne-1,4-diol which can be hydrogenated further to form butanediol.

Aromatic compounds such as benzene, aniline or toluidine, which form the corresponding diphenylmethane derivatives, e.g. diaminodiphenylmethane (MDA).

Olefins, which enable α-hydroxymethyl compounds to be prepared in an acid-catalyzed Prins reaction; where the aromatic compounds and olefins may in each case bear other or no functional groups in addition to or in place of the functional groups mentioned.

Further important reactions are the trimerization of formaldehyde to form trioxane. Here, the aqueous formaldehyde solution of the present invention is reacted in a reactor in the presence of an acid catalyst. A trioxane/formaldehyde/water mixture is separated off, concentrated and trioxane is extracted therefrom by means of an inert solvent. The water/formaldehyde fraction is recycled to the beginning of the process. The use of the aqueous formaldehyde solutions of the present invention is particularly advantageous in this reaction because of the high concentration and the low water content, since a great deal of energy is required for vaporizing water in this process.

The polymerization of formaldehyde or cyclic acetals such as 1,3,5,-trioxane leads to polyoxymethylenes (POMs). Copolymerization of trioxane with cyclic ethers, e.g. ethylene oxide, leads to formation of modified POMs. Such POMs can be prepared from the aqueous formaldehyde solutions of the present invention by gas-phase, precipitation, solution or bulk polymerization.

Many synthetic polymers (synthetic resins) can be prepared by condensation of the aqueous formaldehyde solutions of the present invention with urea, melamine (as already mentioned above), urethanes, cyanamide, aromatic sulfonamides, amines and phenol.

Furthermore, glycolic acid can be prepared from the aqueous formaldehyde solutions of the present invention and CO. Reaction of hydrocyanic acid with the aqueous formaldehyde solutions of the present invention enables glycol nitriles to be prepared.

This listing is not exhaustive. Textbooks on organic chemistry and industrial chemistry (e.g. Ullmann's Encyclopedia of Industrial Chemistry, 6th Edition, 2000 electronic release, keyword: formaldehyde; chapter 3 (Chemical Properties) or J. Frederic Walker "Formaldehyde"/American Chemical Society monographs series 1964) give further examples of reactions. However, this listing is intended to illustrate, by way of example, the industrial importance of formaldehyde as a building block in the overall field of organic synthesis. This applies both to small-tonnage intermediates in the pharmaceuticals or crop protection sectors, e.g. oximes, and to large-tonnage products such as diphenylmethane derivatives.

The present invention therefore also provides for the use of the aqueous formaldehyde solutions of the present invention for preparing synthetic polymers (e.g. synthetic resins, amino resins); for preparing fertilizers; for the synthesis of numerous organic compounds (e.g. hexamethylenetetramine, polyhydric alcohols such as pentaerythritol, trimethylolpropane, neopentyl glycol, diphenylmethane derivatives, oximes, cyclic ethers, trioxane and butynediol, α-hydroxymethyl compounds, glycol nitrites); for preparing dyes (e.g. fuchsin); in wood glues as phenol-formaldehyde resin and for preparing polyoxymethylene and modified polyoxymethylenes.

It is possible to use the aqueous formaldehyde solutions of the present invention in all the abovementioned preparative processes. Compared to the use of the aqueous formaldehyde solutions employed hitherto, the water load is significantly reduced, as a result of which the space-time yield is increased and the capital costs are reduced by the use of smaller apparatuses. The amount of wastewater obtained is reduced and energy savings are achieved in the thermal removal of water.

The following examples illustrate the invention.

EXAMPLES

Preparation of high-concentration formaldehyde solutions in a thin film evaporator:

Via a feed line, a 30% strength by weight raw formaldehyde solution is fed in at 20° C.

Figure 2:
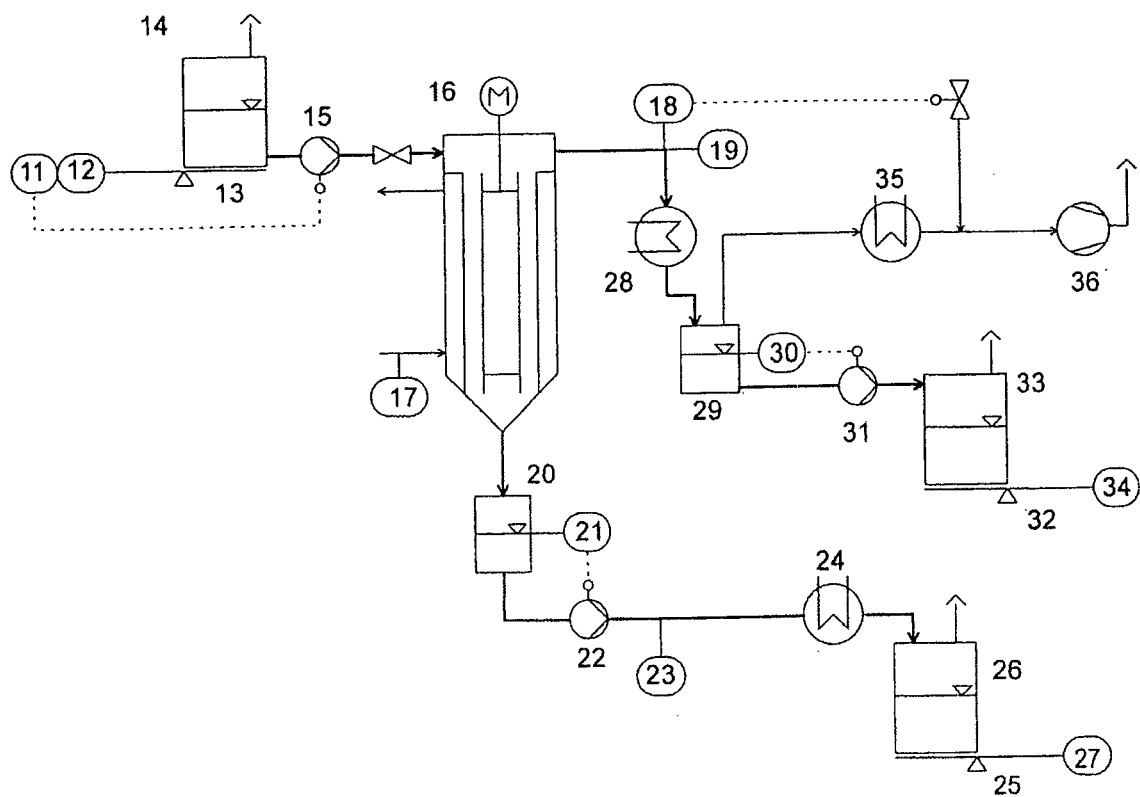

FIG. 2 shows a laboratory setup comprising a film evaporator for the preparation of high-concentration formaldehyde solutions.

The reference numerals in this figure have the following meanings:

| | |
|---|---|
| 11 | flow regulator and display |
| 12 | weighing with display and recorder |
| 13 | balance 1 |
| 14 | vessel 1 |
| 15 | pump 1 |
| 16 | film evaporator |
| 17 | temperature measurement point with display, recorder and regulator |
| 18 | pressure measurement with display, recorder and regulator |
| 19 | temperature measurement point with display and recorder |
| 20 | vessel 2 |
| 21 | fill level measurement with display and regulator |
| 22 | pump 2 |
| 23 | analysis with display and recorder |
| 24 | heat exchanger 1 |
| 25 | balance 2 |
| 26 | vessel 3 |
| 27 | weighing with display and recorder |
| 28 | heat exchanger 2 |
| 29 | vessel 4 |
| 30 | fill level measurement with display and regulator |
| 31 | pump 3 |
| 32 | balance 3 |
| 33 | vessel 5 |
| 34 | weighing with display and recorder |
| 35 | heat exchanger 3 |
| 36 | vacuum pump 1 |

Example 1

Preparation of a 77% strength by weight formaldehyde solution

| | | Sequential number: | | |
|---|---|---|---|---|
| | | 1 | 2 | 3 |
| | | Description | | |
| | | Feed | Bottoms | Condensate |
| Total amount | g/h | 789.6 | 252.6 | 537.0 |
| Amount of water | g/h | 552.7 | 58.1 | 494.6 |
| Amount of $CH_2O$ | g/h | 236.9 | 194.5 | 42.4 |
| Concentration of $CH_2O$ | g/g | 0.30 | 0.77 | 0.079 |
| Parameter: | | | | |
| Pressure | mbar | 70 | | |
| Speed of rotation | 1/min | 400 | | |
| Temperature | °C. | 47.9 | | |
| Temperature of heating jacket | °C. | 90.0 | | |
| Temperature of condenser | °C. | 2.0 | | |

Example 2

Preparation of a 69% strength by weight formaldehyde solution

| | | Sequential number: | | |
|---|---|---|---|---|
| | | 1 | 2 | 3 |
| | | Description | | |
| | | Feed | Bottoms | Condensate |
| Total amount | g/h | 1027.2 | 245.3 | 781.9 |
| Amount of water | g/h | 816.6 | 76.0 | 740.5 |
| Amount of $CH_2O$ | g/h | 210.6 | 169.3 | 41.4 |
| Concentration of $CH_2O$ | g/g | 0.205 | 0.690 | 0.053 |
| Parameter: | | | | |
| Pressure | mbar | 80 | | |
| Speed of rotation | 1/min | 400 | | |
| Temperature | °C. | 64.5 | | |
| Temperature of heating jacket | °C. | 95 | | |
| Temperature of condenser | °C. | 3 | | |

We claim:

1. An aqueous formaldehyde solution comprising formaldehyde in the form of monomeric formaldehyde, methylene glycol and polyoxymethylene glycols in a total concentration x of ≧65% by weight, wherein the mean molar mass $\overline{M}$ of the polyoxymethylene glycols is, as a function of the formaldehyde concentration, equal to or less than the values given by equation I:

$$\left(\frac{\overline{M}}{g/mol}\right) = 48 + 6.589 \cdot 10^{-1} \cdot \left(\frac{x}{\% \text{ by weight}}\right) + 4.725 \cdot 10^2 \cdot \left(\frac{x}{\% \text{ by weight}}\right)^2 - 3.434 \cdot 10^{-3} \cdot \left(\frac{x}{\% \text{ by weight}}\right)^3 + 9.625 \cdot 10^{-5} \cdot \left(\frac{x}{\% \text{ by weight}}\right)^4 - 1.172 \cdot 10^6 \cdot \left(\frac{x}{\% \text{ by weight}}\right)^5 + 5.357 \cdot 10^{-9} \cdot \left(\frac{x}{\% \text{ by weight}}\right)^6 \quad (I)$$

where:

$\overline{M}$ is the mean molar mass, and x is the total concentration of formaldehyde in the form of monomeric formaldehyde, methylene glycol and polyoxymethylene glycols in % by weight (total formaldehyde concentration).

2. An aqueous formaldehyde solution as claimed in claim 1, wherein no precipitation of solids occurs within a period of at least 5 seconds.

3. An aqueous formaldehyde solution as claimed in claim 1 which further comprises stabilizers selected from among methanol, ethanol, propanol, butanol, urea and melamine.

4. A process for preparing an aqueous formaldehyde solution as claimed in claim 1 by thermal separation in one stage of an aqueous formaldehyde solution comprising from 5 to 65% by weight of a starting mixture of formaldehyde in the form of monomeric formaldehyde, methylene glycol and polyoxymethylene glycols and optionally further components such as stabilizers, in which the aqueous formaldehyde solution is at least partly vaporized, into at least two fractions in which various compounds of the mixture are present in higher concentrations than in the starting mixture, where at least one of the two or more fractions is depleted in water compared to the starting mixture so that the formaldehyde in the form of monomeric formaldehyde, methylene glycol and polyoxymethylene glycols is present in this fraction in a total concentration of ≧65% by weight, wherein no aging at elevated temperatures of the fraction wherein the formaldehyde is present in form of monomeric formaldehyde, methylene glycol and polyoxymethylene glycol in a total concentration of ≧65% by weight is carried out after the separation.

5. A process as claimed in claim 4, wherein the separation is carried out within a period of from 1 second to 5 hours.

6. A process as claimed in claim 4, wherein the at least partial vaporization is carried out in a film evaporator.

7. A process as claimed in claim 4, wherein the at least partial vaporization is carried out in a reaction column.

8. A process as claimed in claim 4, wherein the thermal separation is carried out at from 10 to 150° C.

9. A process for preparing monomeric, oligomeric and polymeric reaction products of monomeric formaldehyde, methylene glycol and/or polyoxymethylene glycols, the process comprising contacting the aqueous formaldehyde solution of claim 1 with compounds reactive with at least one of monomeric formaldehyde, methylene glycol and polyoxymethylene glycols.

10. A process as claimed in claim 9, wherein said compounds reactive with monomeric formaldehyde, methylene glycol and polyoxymethylene glycols are selected from the group consisting of compounds containing amino groups; alcohols, thiols, carboxylic acids, diols, aldehydes (including formaldehyde itself); malonates; ketones; hydroxylamines, hydrazines, semicarbazides; acetylene and aromatic compounds and olefins which may in each case bear other or no functional groups in addition to or in place of the functional groups mentioned.

11. An aqueous formaldehyde solution as claimed in claim 1, wherein no precipitation of solids occurs within a period of at least 1 minute.

12. An aqueous formaldehyde solution as claimed in claim 1, wherein no precipitation of solids occurs within a period of at least 5 minutes.

13. An aqueous formaldehyde solution as claimed in claim 1, wherein no precipitation of solids occurs within a period of at least 1 hour.

14. An aqueous formaldehyde solution as claimed in claim 6, wherein the film evaporator is selected from the group consisting of among thin film evaporators, helical tube evaporators, coil tube evaporators and falling film evaporators.

* * * * *